(12) United States Patent  (10) Patent No.: US 7,060,070 B1
Anastopoulos et al.  (45) Date of Patent: Jun. 13, 2006

(54) LOCKING NAIL AND AIM-TAKING APPARATUS

(75) Inventors: George Anastopoulos, Athens (GR); Paul Bernd Robioneck, Preetz (DE)

(73) Assignee: Stryker Trauma GmbH (DE)

( * ) Notice: Subject to any disclaimer, the term of this patent is extended or adjusted under 35 U.S.C. 154(b) by 613 days.

(21) Appl. No.: 10/203,492

(22) PCT Filed: Oct. 10, 2000

(86) PCT No.: PCT/EP00/09935

§ 371 (c)(1),
(2), (4) Date: Nov. 15, 2002

(87) PCT Pub. No.: WO01/60272

PCT Pub. Date: Aug. 23, 2001

(30) Foreign Application Priority Data

Feb. 19, 2000 (DE) .......................... 200 03 053 U

(51) Int. Cl.
*A61B 17/72* (2006.01)
*A61B 17/17* (2006.01)

(52) U.S. Cl. .......................................... 606/64; 606/98

(58) Field of Classification Search .................. 606/62, 606/64, 96, 98
See application file for complete search history.

(56) References Cited

U.S. PATENT DOCUMENTS

| 2,812,761 | A | * | 11/1957 | Palkovitz ..................... 606/98 |
| 4,697,585 | A | | 10/1987 | Williams |
| 5,176,681 | A | | 1/1993 | Lawes et al. |
| 5,454,813 | A | | 10/1995 | Lawes |
| 5,658,287 | A | | 8/1997 | Hofmann et al. |
| 6,039,739 | A | | 3/2000 | Simon |
| 6,136,037 | A | | 10/2000 | Hässig et al. |

FOREIGN PATENT DOCUMENTS

| EP | 0 355 411 | 2/1990 |
| EP | 0 715 832 A2 | 6/1996 |

OTHER PUBLICATIONS

The Journal of Trauma, vol. 35, No. 5, Nov., 1993, pp. 772-775.

* cited by examiner

*Primary Examiner*—David O. Reip
(74) *Attorney, Agent, or Firm*—Lerner, David, Littenberg, Krumholz & Mentlik, LLP

(57) ABSTRACT

A locking nail for treating fractures of tubular bones has two parallel cross-bores that are axially spaced apart provided on the distal end of said nail and optionally at least one additional cross-bore is provided on the proximal end thereof for receiving bone screws. The nail includes a groove which is parallel to a longitudinal axis of the nail is formed into the outer side of the nail. The groove extends into the distal bores on both sides and merges into the bore. The longitudinal axis of the groove intersects the axis of each cross-bore.

17 Claims, 2 Drawing Sheets

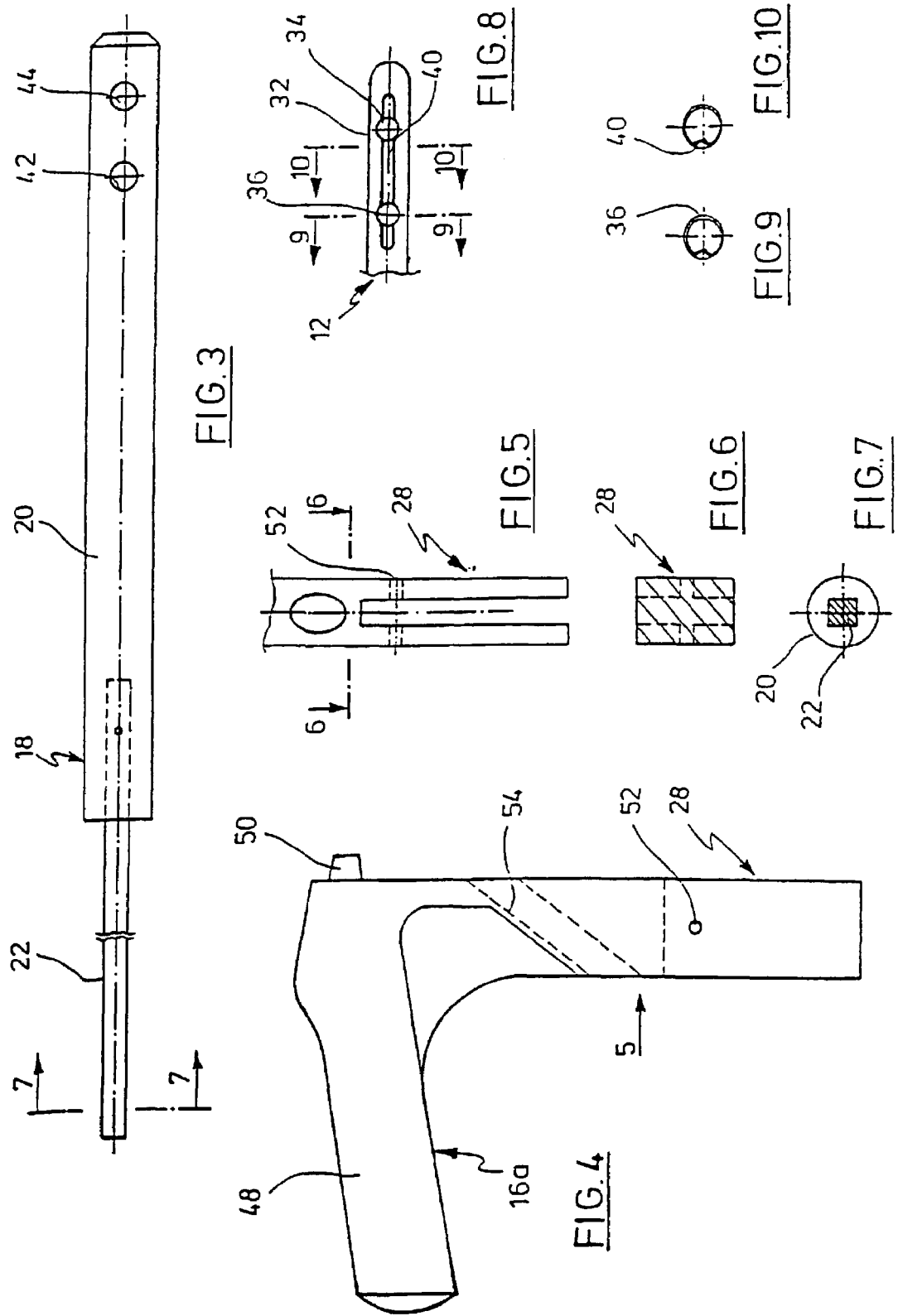

LOCKING NAIL AND AIM-TAKING APPARATUS

BACKGROUND OF THE INVENTION

This invention relates to a bone nail and a targeting device for locating cross-locking holes in the bone nail.

Locking nails to care for fractures in cylindrical hollow bones are widely used. Their utilization is described, for example, in "The Journal of Trauma" of 1993, Vol. 35, No. 5, pp. 772 to 775. It is the typical of such locking nails that two cross-bores are disposed at the distal end and at least one cross-bore is disposed at the proximal end. Bone screws are passed through the cross-bores. They are screwed into the corticalis at opposed sides. This secures the locking nail axially and against a rotation.

A problem in employing such locking nails is how to identify the position of the cross-bores to drill a hole in the corticalis in the right place from outside. A number of aim-taking apparatus has become known, which work with X-rays to identify the position of the cross-bores relative to an aiming or targeting apparatus. Therefore, it is possible to drill a hole in the bone in the right place by means of the targeting apparatus and a so-called drilling sleeve or targeting sleeve. In most cases of the known targeting instruments are firmly connected to the proximal end of the nail. Such an instrument is shown in U.S. Pat. Nos. 5,176,681 and 5,454,813. Thus, the position of the cross-bores may already be preset in an approximately precise way. However, it should be considered that the presumed position of the cross-bores does not coincide with the real one because of the curvature of the bone and the possible torsion of the nail while it is driven in.

Although the position of the cross-bores may be determined by means of X-rays in a relatively precise way using X-rays is not always the best means of choice because it could cause harm to both the patient and surgeon. Therefore, it has also become known to employ targeting apparatus not including X-raying equipment. As mentioned earlier the approximate position of the cross-bores already results from the distance at which the holes are spaced from the proximal end and the circumferential position results from given markings at the proximal end of the locking nail, which cause the targeting apparatus to be connected to the nail in a given rotational position. As explained earlier, however, it is impossible to precisely identify the position of the cross-bores only in a mechanical way by using the known means.

SUMMARY OF THE INVENTION

It is the object of the invention to provide a locking nail which makes it possible to easily determine the position of the distal cross-bores even without using X-raying equipment.

According to the invention, an axially parallel groove is formed in the outside of the nail. It extends at either side of at least that cross-bore which is positioned nearest to the distal end of the nail. The longitudinal axis of the groove intersects the axis of the bone nearly perpendicularly. In an aspect of the invention, the groove is preferably U-shaped in cross-section and is preferably rounded at bottom. Preferably, the groove extends beyond the two cross-bores in the distal and proximal directions. The maximum width of the groove may be smaller than the diameter of the cross-bores. Preferably, the distal end of the locking nail is of a cylindrical shape. The end may be hollow or massive depending on choice.

Conventional targeting apparatus are located axially and with respect to their relative rotational position at the proximal end of the locking nail. Hence, the position of the outermost distal cross-bore may be preset in a nearly approximate way. This can be done in the same way in the inventive locking nail. After the approximate position is found a hole may be cortically drilled in the bone following an incision puncture. However, it is only the associated bone wall which is drilled open. Subsequently, a drill smaller in diameter or a wire pin or the like is passed through the hole in the bone. The operator may now make out by sensing whether the pin may be readily inserted by passing it through the distal cross-bore. If this is not the case he may find out whether he has got the inner end of the pin into the groove. He can find it out particularly by slightly turning the locking nail by means of the targeting apparatus which is still mounted on the nail. This enables him to adjust the rotational position of the locking nail with regard to the hole drilled in the bone already. Now, in order to obtain an alignment of the cross-bore towards the bone hole also in an axial direction the nail is driven in slightly more or is pulled out a little bit by means of the targeting apparatus until the right position of the cross-bore is adjusted.

It is very unlikely that the locking nail will be deformed in the region between the two distal cross-bores to such an extent that the original position of the two cross-bores relative to each other would be changed. Hence, once the position of the first cross-bore is determined the position of the second bore is fixed as well. Therefore, the inventive locking nail can be used the threadably connect the distal end of the locking nail in a simple way with no recourse to X-raying equipment.

However, the invention provides a suitable targeting apparatus with a view to readily localizing the second cross-bore in the locking nail as well in order that the second hole may be drilled in the bone in the right place. It has a handle portion which is adapted to conventionally be connected to the proximal end of the locking nail in order to fix it to the locking nail in the axial and rotational directions. Connectable to the handle portion is also an targeting bar, which is releasably mountable on the handle portion, but is located, when mounted, in an axially and rotationally stable condition. The targeting bar extends in parallel with and at a distance from the locking nail when the latter is mounted on the handle portion. Thus, the targeting bar externally extends in parallel with the length of the bone of which requires to be cared for. Distally, the targeting bar has two cross-bores the distance between which corresponds to the cross-bores of the locking nail. Still, they are larger in diameter as is known as such in order to receive a drilling or aiming sleeve. What is substantial for the invention, however, is that the distal portion of the targeting bar is made of a resilient material, preferably an appropriate plastic material which preferably is PTFE.

The distal portion is preferably formed cylindrically. On the contrary, the proximal part of the targeting bar consists of a relative rigid material which is a metal, for example, to permit its rotationally stable reception in the handle portion.

According to the above-described procedure, when a bone screw is screwed into the most distally located cross-bore of the locking nail the distal bar may be slipped subsequently onto the shank of the screw-driver which is still connected to the bone screw. The proximal end of the targeting bar, however, is connected to the handle portion of the targeting apparatus in its given rotational position. If a torsion of the locking nail has occurred while it was driven in the targeting bar will automatically undergo a torsion, too. This torsion will take place, first and foremost, in the resilient distal portion, the consequence of which is that also the second cross-bore of the aim-taking bar is now aligned more precisely towards the second cross-bore of the aim-taking nail. There is a similar case when the nail has been bent in the bone. The distal bar portion will then be subjected to bending as well. Therefore, it is now possible to drill the second hole in the bone by means of the second cross-bore of the distal portion and to insert the second bone screw subsequently.

BRIEF DESCRIPTION OF THE DRAWINGS

The invention will now be explained with reference to the drawings.

FIG. 3 is a side view of the targeting bar of the aim-taking apparatus of FIGS. 1 and 2;

FIG. 4 is a side view of the handle portion which is modified as compared to one of FIGS. 1 and 2;

FIG. 5 shows a part of the handle portion of FIG. 4 in a side view according to arrow 5;

FIG. 6 shows a section through the representation of FIG. 5 along lines 6—6;

FIG. 7 shows a section through the targeting bar of FIG. 3 along the lines 7—7;

FIG. 8 shows the distal end of the locking nail according to the invention;

FIG. 9 shows a section through the nail portion of FIG. 8 along lines 9—9; and

FIG. 10 shows a section through the nail portion of FIG. 8 along lines 10—10.

DESCRIPTION OF THE PREFERRED EMBODIMENT

Figure 1:
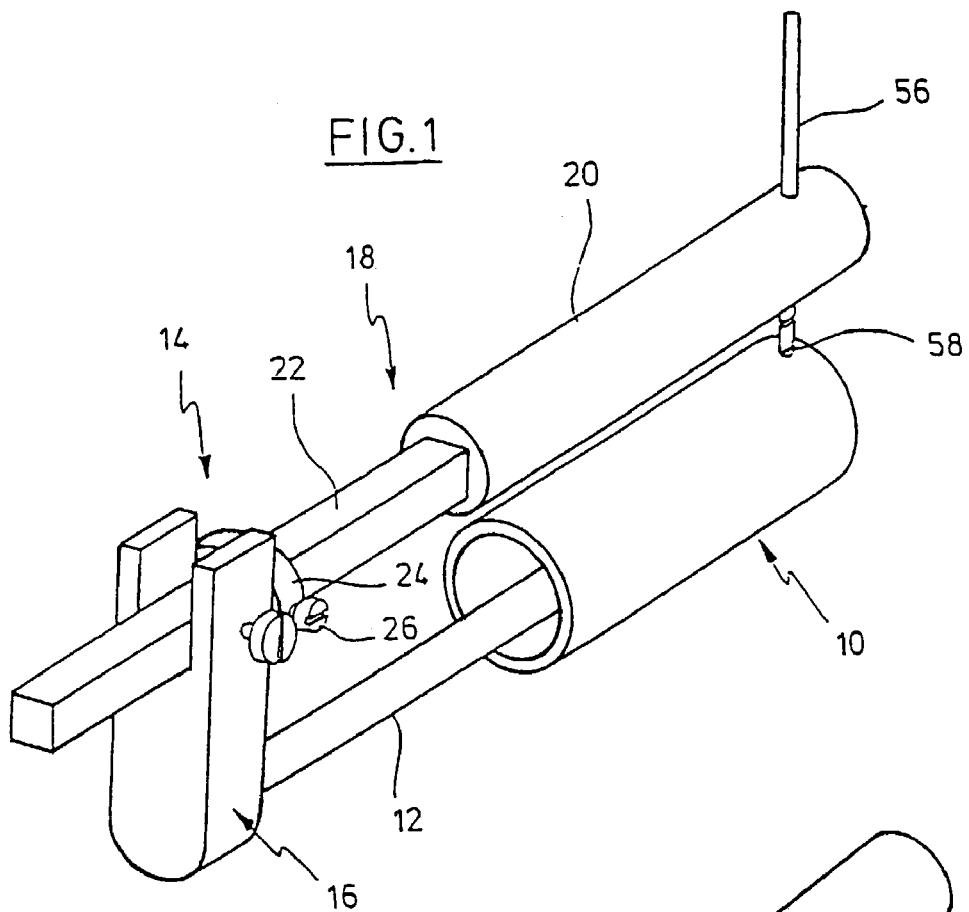
FIG. 1 is a schematic perspective view of a targeting apparatus according to the invention and a bone nail in a cylindrical hollow bone which is schematically outlined.

Referring to FIG. 1, a cylindrical hollow bone 10 is outlined which requires to be cared for by means of a locking nail 12 which is only outlined as well. A targeting apparatus 14, which is outlined in FIG. 1, has a handle portion 16 to which the proximal end of nail 12 is connected in an axially and rotationally stable way. The type of connection is not shown. It is known per se. A targeting bar 18, which consists of a distal portion 20 and a proximal portion 22, extends in parallel with nail 12. Proximal portion 22 is a metallic square. Distal portion 20 is cylindrical and is formed from an elastic plastic material such as PTFE. Portions 20, 22 are interconnected in an appropriate way which, however, is not shown. Seated in a rotationally stable way on portion 22 of targeting bar 18 is a fixing ring 24 which, however, is axially displaceable with the axial position being locatable by means of a fixing screw 26. Handle portion 16 has a bifurcated portion 28 where the gap between its legs is sized so as to fittingly receive square portion 22. Another fixing screw 30 serves for locating square portion 22 in bifurcated portion 28.

Figure 2:
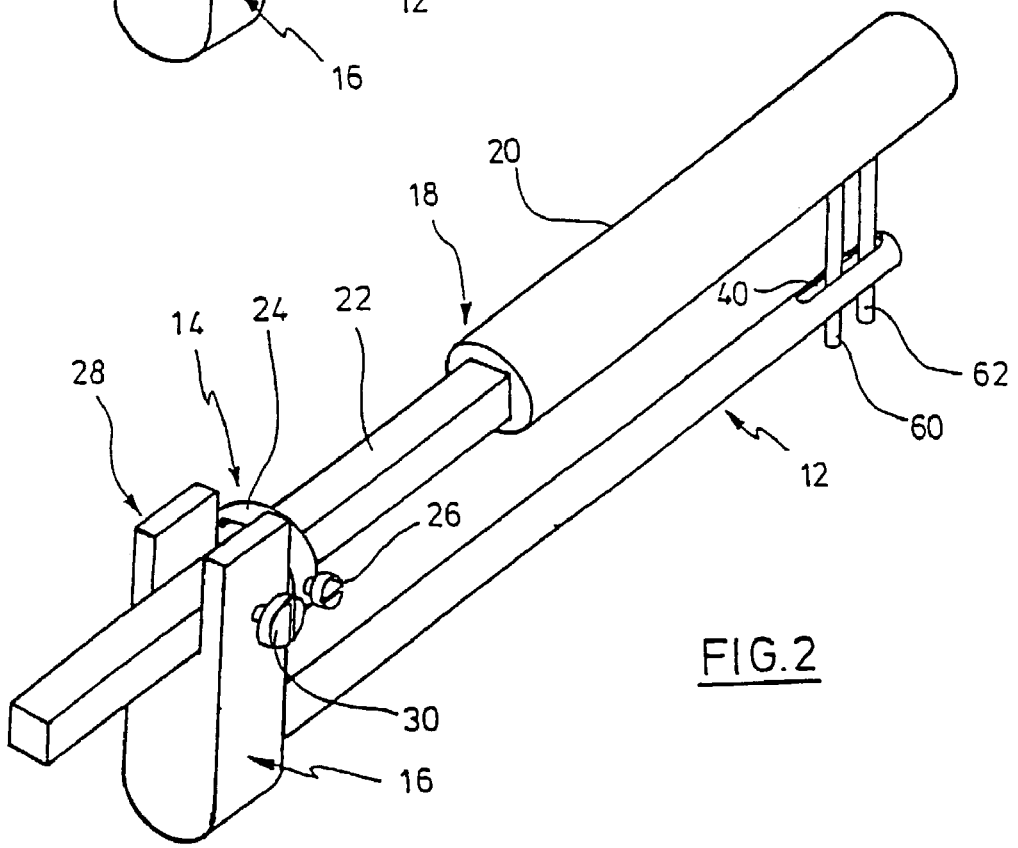
FIG. 2 is an schematic perspective view of the aim-taking apparatus of FIG. 1 in its complete shape.

As is evident from FIG. 2 locking nail 22 is provided with two distal cross-bores as is known as such. This is more obvious from the representation of FIG. 8. The distal portion of the locking nail is indicated by 32 and the cross-bores are given the reference numbers 34 and 36. What is apparent from a consideration of FIGS. 2 and 8 to 10 is that the distal portion 32 has externally formed therein a groove 40 which runs in an axially parallel direction thereto and extends beyond bores 34, 36 in the distal and proximal directions, respectively. Its extension along the two sides of bores 34, 36 is 5 mm, for example. In addition, groove 40 extends into bores 34, 36. It is evident from FIGS. 9 and 10 that the groove is approximately U-shaped in cross-section and is rounded at bottom. It is slightly smaller in width than the diameter of cross-bores 34, 36.

Targeting bar 18 is shown in a slightly more distinct way in FIGS. 3 and 7. It can be seen, for instance, that square portion 22 is partly embedded in the material of distal portion 20. On the distal side, distal portion 20 has two cross-bores 42, 44. The distance of their axes corresponds to the distance of the axes of cross-bores 36, 34 (the drawings not being to scale). The diameter of cross-bores 42, 44 is larger than the diameter of cross-bores 34, 36 because they also require to receive a sleeve through which a drill can be introduced, reference to which will be made further below.

Handle portion 16a of FIG. 4 distinguishes itself from the one of FIGS. 1 and 2 in that it is angle-shaped. It has a cone 50, onto which the locking nail (not shown) is slipped, at the right-hand upper end of handle 48. The other mounting of the locking nail is not described as was mentioned earlier.

Like handle portion 16, handle portion 16a has a bifurcated portion 28 to fittingly receive square portion 22. Referring to FIG. 5, a threaded through cross-bore 52 can be seen for receiving the fixing screw 30 of FIG. 2.

Handle portion 16a has an oblique through bore 54 above bifurcated portion 28 with no reference being made to its function.

When an implantation is made and cross-bores 34, 36 of locking nail 12 are discovered subsequently the distance of these cross-bores from the proximal end is known for the nail which is not yet driven in. Therefore, targeting bar 18 may be mounted in its axial position in such a way that its cross-bores 42, 44 are aligned towards the presumed position of the locking nail which was implanted or towards its cross-bores 34, 36. In practice, however, the real position of cross-bores 34, 36 may deviate therefrom because locking nail 12 has been bent or there is a torsion. In any case, the targeting procedure is initially based on the presumed position. In this position, a hole 58 is drilled in bone 10 by means of a drill 56 of FIG. 1, i.e. merely in the associated wall of the bone. Targeting bar 18 will then be removed. After this, the operator manually introduces a drill which is smaller in diameter (he perhaps used a 5.5 mm drill before the succeeding drill and the pins are 3.5 mm in diameter) into the bone hole until it feels the nail. If the operator does not feel the cross-bore 34 he slightly rotates nail 12 until the operator makes out groove 40 by sensing. Nail 12 is then moved on and back until it is possible to further introduce the drill shank or wire pin with ease. After this, a hole may also be drilled in the opposed corticalis and the bone screw may be screwed in subsequently. The shank of the screw-driver remains on the screw, and targeting bar 18 is then located in handle portion 16 and 16a, respectively, in a repeatable position. This will possibly torsion or deform distal portion 20 if the nail also sustained a deformation or torsion while being driven in. Second cross-bore 42 of distal portion 20 is then precisely aligned with second cross-bore 36 of nail 12 so that a hole may also be drilled now in the corticalis for the second cross-bore 36 for a subsequent screw-connecting operation by means of the second bone screw which is not shown.

FIG. 2 is intended to merely outline the interaction of targeting screw 18 and cross-bores 34, 36 of nail 12 by means of pins 60, 62 which are shown.

Subsequently, locking nail 12 may also be locked in a manner which is known per se. It is unlikely that a deformation has occurred in this region. Hence, a hole provided on targeting bar 18 (not shown) coincides with the proximal cross-bore of nail 12 in any case. Thus, no difficulties will be encountered by the operator.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A locking nail for treating a fracture in a long bone comprising a proximal and a distal portion, said distal portion having two cross-bores spaced in the axial direction with respect to a longitudinal axis of the nail, said cross-bores extending generally perpendicular to said longitudinal axis, said distal portion having a surface including a groove extending between the two cross-bores and extending parallel to said longitudinal axis, said groove having first and second ends wherein the first and second ends are spaced about 5 mm from the two cross-bores in the proximal-distal direction.

2. The locking nail according to claim 1, wherein the distal portion of the nail is of a cylindrical shape.

3. The locking nail according to claim 1, wherein the groove has a cross-section smaller than the diameter of the cross-bores.

4. A targeting apparatus for a locking nail having at least two distal cross-bores for receiving cross-locking screws, said apparatus comprising:
a handle portion having a means for engaging the nail and for locating the proximal end of the locking nail in the axial and rotational directions;
a targeting arm releasably having a proximal portion attached to one end of the handle portion and when attached thereto being fixed axially and rotationally thereto, said arm being spaced from and extending in parallel with a longitudinal axis of the locking nail, the arm having at least two cross-bores in a distal portion, which can be aligned with the cross-bores in the locking nail, said distal end adjacent said cross-bores formed of a resilient material capable of deforming under loads placed thereon by a cross-locking screw.

5. The targeting apparatus according to claim 4, wherein the distal portion is formed from a resilient plastic material.

6. The targeting apparatus according to claim 5, wherein the distal portion is a cylinder.

7. The targeting apparatus as set forth in claim 5, wherein the plastic is polyethylene.

8. The targeting apparatus according to claim 4, wherein the proximal portion of the targeting arm is formed from a relatively rigid material and is non-circular in cross-section at a proximal end for its rotational fixation in a complementary recess or opening in the handle portion.

9. The targeting apparatus according to claim 8, wherein the non-circular cross-section is a square and the handle portion has a bifurcated portion having legs which fittingly accommodate said square cross-section and at least one leg of the bifurcated portion has a threaded bore to receive a set screw for releasably clamping said proximal arm portion.

10. A method for locating cross-bores in a distal end of a locking nail for healing bone fractures comprising:
inserting a locking nail having a longitudinal axis and a pair of cross-bores in a distal end thereof and an external groove parallel to the longitudinal axis connecting the cross-bores;
fixing a targeting device to a proximal portion of the locking nail, the targeting device including a targeting arm extending parallel to the longitudinal axis of the locking nail and having a distal portion with cross-bores;
selectively preventing the targeting device from moving axially and rotationally with respect to said nail;
inserting a pin through a cross-bore in the targeting arm; and
locating the groove in the nail with the pin and locating the cross-bore by axially moving said targeting arm parallel to the longitudinal axis with the pin in the groove.

11. The method as set forth in claim 10, wherein the distal portion of said targeting arm surrounding said cross-bores is resilient.

12. The method as set forth in claim 11 further comprising resiliently deforming the distal portion of the arm by inserting a screw through a related cross-bore in said arm and said nail.

13. The method as set forth in claim 10, wherein said groove extends beyond said locking nail cross-bores in the proximal and distal directions.

14. A method for locating a cross-bore in a distal end of a locking nail for healing bone fractures comprising:
inserting a locking nail having a longitudinal axis and a pair of cross-bores in a distal end thereof and an external groove parallel to the longitudinal axis connecting the bores;
fixing a targeting device to a proximal portion of the locking nail, the targeting device including a targeting arm extending parallel to the longitudinal axis of the locking nail and having a distal portion with cross-bores, said distal portion being resilient; and
inserting a pin through a cross-bore in the targeting arm into a cross-bore by deforming the resilient distal portion of the targeting arm.

15. The method as set forth in claim 14, wherein said distal portion of said targeting arm is made of polyethylene.

16. The method as set forth in claim 14, wherein said locking nail includes a groove extending parallel to said longitudinal axis connecting said bores and said cross-bores in said nail are located by engaging said pin with said groove and axially moving said targeting arm until said pin engages said cross-bore.

17. The method as set forth in claim 16, wherein said groove extends beyond said locking nail cross-bores in the proximal and distal directions.

* * * * *